United States Patent [19]

Malguarnera

[11] Patent Number: 4,641,535
[45] Date of Patent: Feb. 10, 1987

[54] FLOWMETER
[75] Inventor: Salvatore C. Malguarnera, Houston, Tex.
[73] Assignee: NL Industries, Inc., New York, N.Y.
[21] Appl. No.: 750,097
[22] Filed: Jun. 28, 1985
[51] Int. Cl.[4] .......................... G01F 1/36; G01N 9/26; G01N 11/04
[52] U.S. Cl. .................................. 73/861.01; 73/198; 73/861.52; 73/32 R; 73/55
[58] Field of Search ................ 73/32 R, 55, 198, 438, 73/195, 861.01, 861.02, 861.03, 861.04, 861.52

[56] References Cited
U.S. PATENT DOCUMENTS 1,863,090  6/1932  Albersheim et al. ............... 73/55
2,023,568 12/1935  Albersheim et al. ............... 73/55
3,487,688  1/1970  Magliozzi ....................... 73/861.52
3,839,914 10/1974  Modisette et al. ................ 73/438
3,926,050 12/1975  Turner et al. .................... 73/861.04
3,952,577  4/1976  Hayes et al. ..................... 73/55
4,231,262 11/1980  Boll et al. ...................... 73/861.04

Primary Examiner—Herbert Goldstein
Attorney, Agent, or Firm—Browning, Bushman, Zamecki & Anderson

[57] ABSTRACT

A method and apparatus for measuring flow parameters of an unknown fluid uses four pressure sensors at fixed, spaced locations within a cylindrical member having a constricted and a full diameter portion. The constricted portion has a smooth surface of transition at its entry, internal corrugations, and a sharp increase to the full diameter at its exit. There are no moving parts. All flow parameters can be calculated from the four pressure measurements taken at the entry and exit of the constricted portion and two aligned but separated locations spaced from the sharp increase to full diameter.

21 Claims, 2 Drawing Figures

FLOWMETER

BACKGROUND OF THE INVENTION

The present invention relates to a flow meter which will allow determination of density, flow rate, and viscosity of a conceptually incompressible fluid from pressure drop measurements alone.

The flow meters presently available are generally restricted to use with a particular fluid or fluid type or are limited to measuring only one of the three important flow parameters, namely density, flow rate and viscosity.

An example of the prior art can be found in U.S. Pat. No. 3,839,914 which discloses a method and apparatus for continuously determining density, velocity and Fanning friction factor, which is further used to determine the viscosity of a liquid flowing through a closed container. The liquid is caused to flow through a conduit having a curved portion and pressure sensors are mounted on both sides of the curved portion to determine the difference in pressure between the fluid flowing adjacent to the inside and the outside curved portion of the conduit. Further pressure sensors are positioned in the conduit at selected equal distances up stream and downstream of the sensors located in the curved portion of the conduit. The difference in pressure of the fluid between these upstream and downstream locations and between the upstream and downstream locations and the curved portion of the conduit are determined. These pressure determinations are then utilized in equations to determine the desired parameters of density, flow velocity and Fanning friction factor.

SUMMARY OF THE INVENTION

The present invention can be distinguished from the prior art in that it can be used with substantially any fluid system. The density, flow rate and viscosity of a fluid can be determined from pressure measurements which assume no prior knowledge of the fluid. The subject flow meter can be used at any location in a fluid system and can have any orientation. It does, however, require an incompressible, steady flow of fluid and factoring in any angular orientation. The fluids which can be measured would include liquids and those gases with a velocity no more than half the speed of sound, provided the pressure sensing devices are capable of measuring very slight pressure drops. The subject meter is an elongated cylindrical member having a constricted section with internal corrugations, a full width section and four pressure transducers fixed to the walls of the member at spaced locations.

BRIEF DESCRIPTION OF THE DRAWINGS

The present invention will be described by way of example with reference to the accompanying drawings in which.

DETAILED DESCRIPTION OF THE PRESENT INVENTION

Figure 1:
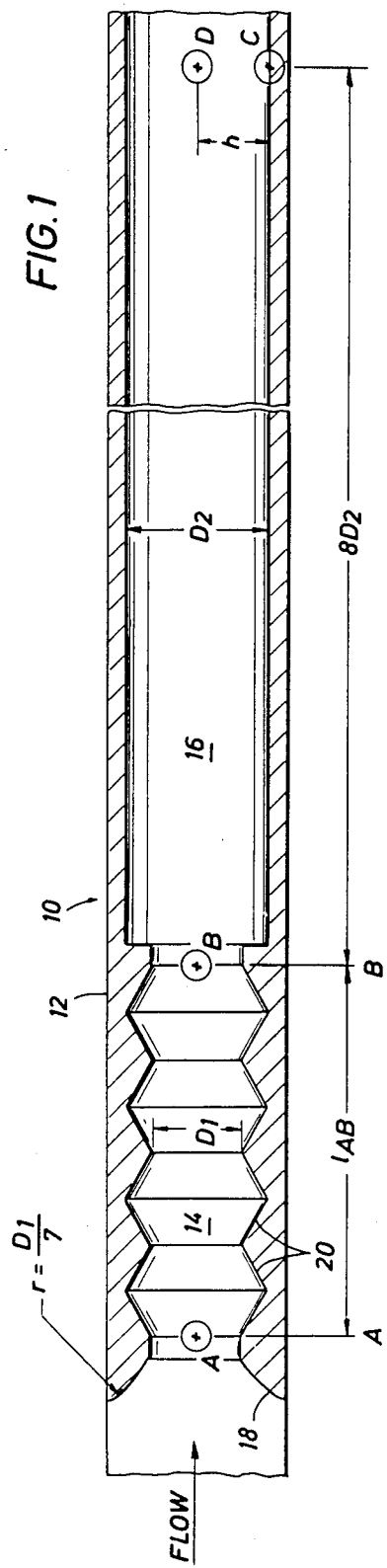
FIG. 1 is a longitudinal section through a flow meter according to the present invention.

An embodiment of the present invention is shown in FIG. 1. The subject flow meter 10 can be made either as an integral part of a longer pipe section or as a tubular member 12 which can be inserted into a larger pipe (not shown), the outer diameter of member 12 forming a close fit with the inner diameter of the larger pipe. The subject flow meter 10 has a constricted diameter section 14 ($D_1$) and an adjacent larger diameter section 16 ($D_2$). The constricted section 14 has an entry 18 which is a smooth surface of transition with a radius approximately equal to one-seventh of the diameter $D_1$ of the constricted section 14. The bore of the section 14 is formed with a continuous series of inwardly directed corrugations 20. A first differential pressure tap A is fixed within the entry end of the constricted section 14 while a second differential pressure tap B is similarly fixed at the exit. The full diameter section 16 has a bore of a second diameter ($D_2$) larger than that of the first diameter $D_1$. Third and fourth differential pressure taps C and D are located in the walls of section 16 a distance of not less than eight times the second diameter ($D_2$) from the interface of the constricted section 14 and the full diameter section 16.

The pressure taps A, B, C and D are all of any of the well known types, such as differential pressure transducers, and are fixed in the walls of their respective sections. Taps C and D are aligned in a transverse plane normal to the axis of the member 12 and tap D is positioned a quarter of the circumference from C so that h, the vertical spacing in a horizontal orientation of the member, equals the radius of the full diameter section 16. Taps B and D are positioned to have the vertical elevation in a gravity field.

The following pressure drops are measured with the differential pressure transducers:

$\Delta P_{AB}$
$\Delta P_{BD}$
$\Delta P_{DC}$ from $\Delta P_{DC}$ $$\Delta P_{DC} = \rho g h$$

where h = the vertical height separating the two pressure tap locations D and C, g is gravity and $\rho$ is density. Thus, the density can be determined by the equation:

$$\rho = \Delta P_{DC}/gh = \text{density}$$

Ignoring the effects of the variation in velocity across the cross section, which would result in a minor correction if included, we can use $\Delta P_{BD}$, the pressure change for a sudden expansion, to obtain the flow rate. The location of the pressure taps C and D must be chosen to be approximately eight diameters ($D_2$) or more downstream of the second pressure tap B.

Considering the control volume shown in FIG. 1, the net force acting to the right is:

$$P_B(\pi D_1^2/4) + P'(\pi/4)(D_2^2 - D_1^2) - P_D(\pi D_2^2/4)$$

where P' represents the mean pressure of fluid eddies in the separate corner regions. It has been shown that $$P' \approx P_B.$$

Thus, the net force is:

$$(P_B - P_D)(\pi D_2^2/4)$$

which equals the rate of change of momentum, where Q is the flowrate.

$$(P_B - P_D)(\pi D_2^2/4) = \rho Q(V_D - V_B)$$

$$(P_B - P_D) = \rho V_D(V_D - V_B)$$

from one energy equation $$\frac{P_B}{\rho g} + \frac{V_B^2}{2g} + Z - h_L = \frac{P_D}{\rho g} + \frac{V_D^2}{2g} + Z$$

$$h_L = \frac{P_B - P_D}{\rho g} + \frac{V_B^2 - V_D^2}{2g}$$

where $h_L$ is the head loss and z is the distance in the gravity field above a datum. Substituting for $(P_B - P_D)$, we get $$h_L = \rho \frac{V_D(V_D - V_B)}{\rho g} + \frac{V_B^2 - V_D^2}{2g}$$

$$= 2V_D^2 - 2V_D V_B + V_B^2 - V_D^2$$

$$= \frac{V_D^2 - 2V_B V_D + V_B^2}{2g} = \frac{(V_B - V_D)^2}{2g}$$

By continuity $$\pi(D_1^2/4)V_B = \pi(D_2^2/4)V_D$$

$$V_B = (D_2^2/D_1^2)V_D$$

$$h_L = \frac{\left(\frac{D_2^2}{D_1^2} V_D - V_D\right)^2}{2g} = \frac{V_D^2\left(\left(\frac{D_2}{D_1}\right)^2 - 1\right)}{2g}$$

$$\rho g h_L = \Delta P_{BD} = \rho \frac{V_D^2}{2}\left(\left(\frac{D_2}{D_1}\right)^2 - 1\right)$$

Thus, $V_D = \sqrt{\dfrac{2\Delta P_{BD}}{\rho\left(\left(\dfrac{D_2}{D_1}\right)^2 - 1\right)}}$ The flowrate Q $$Q = \frac{\pi D_2^2}{4}\sqrt{\frac{2\Delta P_{BD}}{\rho\left(\left(\frac{D_2}{D_1}\right)^2 - 1\right)}}$$

Figure 2:
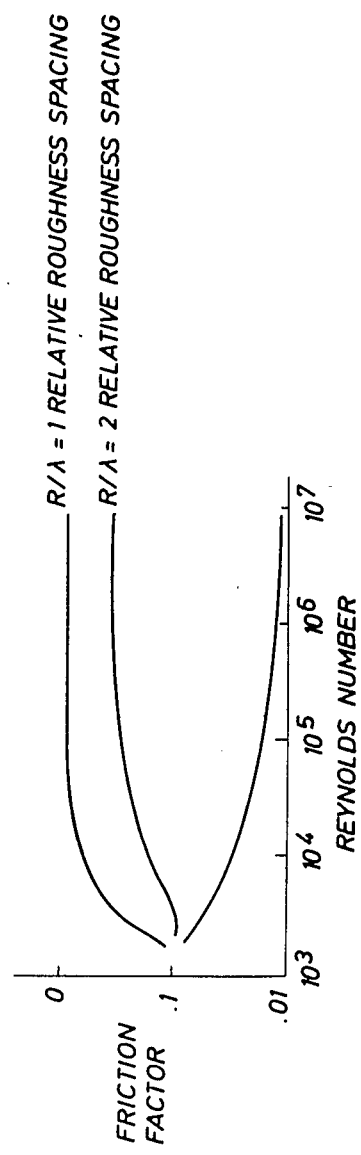
FIG. 2 is a graph showing the friction factor relationship to the Reynolds number.

The density and flow rate have been determined so it is now possible to determine the fluid viscosity. Constricted section 14 has a nominal diameter $D_1$ with a sloped entrance having a radii of 1/7 the diameter $D_1$ in order to eliminate any pressure drop due to flow contraction. The section is machined with regular corrugations of any desired shape and size which will give much higher pressure drops for a given flow rate. The corrugations will also give a predictable, continuous friction factor-Reynolds number relationship which will be a function of the relative roughness spacing. The Reynolds number of a flow is defined as the product of a scale velocity and a scale length divided by the kinematic viscosity of the fluid. As example is shown in the graph of FIG. 2. This curve must be determined empirically for any given number of corrugations, thus shape and depth.

The friction factor f is defined as $$f = \frac{\Delta P}{\frac{1}{2}\left(\frac{L}{D_1}\right)\rho V^2}$$

where L is the length of the conduit with a diameter $D_1$ over which a pressure drop $\Delta P$ is measured. The average velocity is V. Friction factors for corrugated pipes will be much higher than for random spot roughness associated with commercial pipes. Thus, a measurable pressure drop can be obtained in a relatively short section of pipe.

The viscosity of the fluid at the average or ambient temperature in the system may be obtained as follows:

measure $\Delta P_{AB}$ $$f = \frac{\Delta P_{AB}}{\frac{1}{2}\left(\frac{L}{D}\right)\rho V_B^2} \quad V_B = \frac{D_2^2}{D_1^2} V_D$$

from f vs Reynolds curve determine Re $$Re = \rho(V_B D_1/\mu)$$

$$\mu = \rho V_B D_1/Re = \text{viscosity}$$

To show the magnitude of pressures measured assume
$D_2 = 8'' = 20.32$ cm; $h = 4'' = 10.16$ cm
$D_1 = 4'' = 10.16$ cm
$l_{AB} = 2'-2'' = 60.96$ cm
water (at standard temperature and pressure)
$\mu = 1 \times 10^{-2}$ poise = 1 centipoise
$\rho = 1$ gm/cm$^3$; 1 gpm = 63.08 cm$^3$/sec
$Q = 300$ gpm = $1.892 \times 10^4$ cm$^3$/sec $\Delta P_{DC} = \rho g h = (1.0)(981)(10.16)$
dyn/cm$^2 = 9.967 \times 10^3$ dyn/cm$^2 = 0.1445$ psi $$\Delta P_{BD} = \frac{16Q^2}{\pi D_2^4} \rho \frac{\left(\left(\frac{D_2}{D_1}\right)^2 - 1\right)}{2}$$

$$= \frac{(16)(1.892 \times 10^4)^2(1)(3)}{2\pi^2(20.32)^4}$$

$$= 5.11 \times 10^3 \text{ dyn/cm}^2 = 7.40 \times 10^{-2} \text{ psi} = .0740 \text{ psi}$$

$$\Delta P_{AB} = f\frac{1}{2}\frac{(L_{AB})}{D_1}\rho V_B^2$$

$$V_B = \frac{Q}{\pi \frac{D_1^2}{4}} = \frac{1.892 \times 10^4}{\pi \frac{(10.16)^2}{4}} = 2.33 \times 10^2 \text{ cm/sec}$$

$$Re = \rho \frac{V_D}{4} = (1)\frac{(2.32 \times 10^2)(10.16)}{1 \times 10^{-2}} = 2.37 \times 10^5$$

from a typical Reynolds chart
$f = 0.1$ for relative roughness spacing $R/\lambda = 3$ $$\Delta P_{AB} = (0.1)(\tfrac{1}{2})(60.96/10.16)(1)(2.33\times 10^2)^2 = 1.63\times 10^4 \text{ dyn/cm}^2 = 0.236 \text{ psi}$$

The pressure drops in the above example could all be measured by commercially available differential pressure transducers. Full scale readings can be as low as 0.08 psi and increments such as 0.125, 0.2, 0.32, 0.5, 0.8 to full scale are available from a number of companies, e.g. Valedyne, Inc. For mud systems, the pressure drop should be higher than those estimated for water and thus easier to measure.

This technique can be used with any liquid or liquid solid system. Specific systems may require special precautions in order to prevent solids settling or scale from building up and becoming a problem in the corrugations of the constricted section and at the location of the pressure taps. If the subject meter is to be used at an angular orientation other than horizontal, then a correction for differential pressure due to a hydrostatic component would have to be factored in. Since density is measured first, it can be used as a correction for other measurements. The subject invention is economical to fabricate and to operate since it has no moving parts.

What is claimed is:

1. A flowmeter having no moving parts and enabling determination of the density, flow rate and viscosity parameters of an unknown fluid, said flowmeter comprising:
    an elongated cylindrical member defining a constricted portion of a first diameter and an adjacent downstream full diameter portion of a second larger diameter;
    first and second pressure sensors fixed, respectively, at the entry and the exit of said constricted portion; and
    third and fourth pressure sensors fixed in said full diameter portion at a distance of at least eight times the second diameter from the junction of said constricted and said full diameter portions, wherein said fourth pressure sensor is aligned with said third pressure sensor in a plane extending normal to the axis of said meter whereby differential pressure readings can be obtained and used to determine the density, flow rate and viscosity of a fluid passing therethrough.

2. The flowmeter according to claim 1 wherein said constricted portion has a smooth surface of transition of a radius one-seventh of the first diameter forming an entry whereby pressure change due to flow contraction is minimized.

3. The flowmeter according to claim 1 wherein said constricted portion has an internal surface formed by a series of corrugations.

4. The flowmeter according to claim 1 wherein said fourth pressure sensor is spaced from said third pressure sensor such that the vertical spacing between them equals the radius of said second diameter.

5. The flowmeter according to claim 1 wherein said fourth pressure sensor is spaced from said second pressure sensor one-quarter of the circumference of the full diameter portion.

6. The flowmeter according to claim 1 wherein said second and fourth pressure sensors have the same vertical elevation in a field of gravity.

7. The flowmeter according to claim 1 wherein said elongated cylindrical member is integrally formed with a longer section of pipe.

8. The flowmeter according to claim 1 wherein said elongated cylindrical member has an outer diameter allowing said flowmeter to be received with close fit within a larger diameter pipe.

9. The flowmeter according to claim 1 wherein said elongated cylindrical member is integral.

10. The flowmeter according to claim 1 wherein said pressure sensors are differential pressure transducers.

11. A method for determining the density, flow rate and viscosity parameters of a fluid comprising the steps of:
    flowing the fluid through a conduit having a constricted portion of a first diameter ($D_1$) and a full width portion of a larger second diameter ($D_2$);
    determining the pressure of the fluid at a first point at the entry of said constricted portion;
    determining the pressure of the fluid at a second point at the exit of said constricted portion;
    determining the pressure of the fluid at a third point in said full width portion spaced from the exit of said constricted portion;
    determining the pressure of the fluid at a fourth point spaced above and aligned with the third point; and
    determining the density, flow rate and viscosity, respectively, in accordance with the following equations:

$$\rho = \Delta P_{DC}/gh$$

where $\Delta P_{DC}$ is the pressure differential between said third and said fourth points, g is gravity, and h is the vertical spacing between the third and fourth points, $$Q = \frac{\pi D_2^2}{4} \sqrt{\frac{2\Delta P_{BD}}{\rho\left(\left(\frac{D_2}{D_1}\right)^2 - 1\right)}}$$

where $\Delta P_{BD}$ is the pressure differential between the second and fourth points, $$\mu = \rho V_B D_1/\text{Re}$$

where Re is the Reynolds number and $V_B$ is average velocity from the equation $$V_B = \frac{D_2^2}{D_1^2} \sqrt{\frac{2\Delta P_{BD}}{\rho\left(\left(\frac{D_2}{D_1}\right)^2 - 1\right)}}.$$

12. A method for determining the density of a fluid comprising the steps of:
    flowing the fluid through a conduit having a constricted portion of a first diameter ($D_1$) and a full width portion of a larger second diameter ($D_2$);
    determining the pressure of the fluid at a first point at the entry of said constricted portion;
    determining the pressure of the fluid at a second point at the exit of said constricted portion;
    determining the pressure of the fluid at a third point in said full width portion spaced from the exit of said constricted portion;
    determining the pressure of the fluid at a fourth point spaced above and aligned with the third point; and determining the density in accordance with the equation $$\rho = \Delta P_{DC}/gh$$

where $\Delta P_{DC}$ is the pressure differential between said third and said fourth points, g is gravity, and h is the vertical spacing between the third and fourth points.

13. A method for determining the flow rate of a fluid comprising the steps of:
flowing the fluid through a conduit having a constricted portion of a first diameter ($D_1$) and a full width portion of a larger second diameter ($D_2$);
determining the pressure of the fluid at a first point at the entry of said constricted portion;
determining the pressure of the fluid at a second point at the exit of said constricted portion;
determining the pressure of the fluid at a third point in said full width portion spaced from the exit of said constricted portion;
determining the pressure of the fluid at a fourth point spaced above and aligned with the third point; and
determining the flow rate in accordance with the following equation:

$$Q = \frac{\pi D_2^2}{4} \sqrt{\frac{2\Delta P_{BD}}{\rho\left(\left(\frac{D_2}{D_1}\right)^2 - 1\right)}}$$

where $\Delta P_{BD}$ is the pressure differential between the second and fourth points and $\rho$ is the density of the fluid.

14. The method according to claim 13 wherein the density is determined in accordance with the equation $$\rho = \Delta P_{DC}/gh$$

where $\Delta P_{DC}$ is the pressure differential between said third and said fourth points, g is gravity, and h is the vertical spacing between the third and fourth points.

15. A method for determining the viscosity of a fluid comprising the steps of:
flowing the fluid through a conduit having a constricted portion of a first diameter ($D_1$) and a full width portion of a larger second diameter ($D_2$);
determining the pressure of the fluid at a first point at the entry of said constricted portion;
determining the pressure of the fluid at a second point at the exit of said constricted portion;
determining the pressure of the fluid at a third point in said full width portion spaced from the exit of said constricted portion;
determining the pressure of the fluid at a fourth point spaced above and aligned with the third point; and
utilizing the above pressures for determining the viscosity in accordance with the following equation:

$$\mu = \rho V_B D_1/\text{Re}$$

where Re is the Reynolds number and $V_B$ the average velocity in the constricted portion.

16. The method according to claim 15 wherein said velocity is determined from the equation $$V_B = \frac{D_2^2}{D_1^2} \sqrt{\frac{2\Delta P_{BD}}{\rho\left(\left(\frac{D_2}{D_1}\right)^2 - 1\right)}}$$

where $\rho$ is the density of the fluid and $\Delta P_{BD}$ is the pressure differential between the second and fourth points.

17. The method according to claim 16 wherein said density is determined from the equation $$\rho = \Delta P_{DC}/gh$$

where $\Delta P_{DC}$ is the pressure differential between said third and said fourth points, g is gravity, and h is the vertical spacing between the third and fourth points.

18. A method for determining the density and flow rate of a fluid comprising the steps of:
flowing the fluid through a conduit having a constricted portion of a first diameter ($D_1$) and a full width portion of a larger second diameter ($D_2$);
determining the pressure of the fluid at a first point at the entry of said constricted portion;
determining the pressure of the fluid at a second point at the exit of said constricted portion;
determining the pressure of the fluid at a third point in said full width portion spaced from the exit of said constricted portion;
determining the pressure of the fluid at a fourth point spaced above and aligned with the third point; and
determining the density and flow rate in accordance with the following equations:

$$\rho = \Delta P_{DC}/gh$$

where $\Delta P_{DC}$ is the pressure differential between said third and said fourth points, g is gravity, and h is the vertical spacing between the third and fourth points, $$Q = \frac{\pi D_2^2}{4} \sqrt{\frac{2\Delta P_{BD}}{\rho\left(\left(\frac{D_2}{D_1}\right)^2 - 1\right)}}$$

where $\Delta P_{BD}$ is the pressure differential between the second and fourth points.

19. A method for determining the flow rate and viscosity of a fluid comprising the steps of:
flowing the fluid through a conduit having a constricted portion of a first diameter ($D_1$) and a full width portion of a larger second diameter ($D_2$);
determining the pressure of the fluid at a first point at the entry of said constricted portion;
determining the pressure of the fluid at a second point at the exit of said constricted portion;
determining the pressure of the fluid at a third point in said full width portion spaced from the exit of said constricted portion;
determining the pressure of the fluid at a fourth point spaced above and aligned with the third point; and
determining the flow rate and viscosity, respectively, in accordance with the following equations:

$$Q = \frac{\pi D_2^2}{4} \sqrt{\frac{2\Delta P_{BD}}{\rho\left(\left(\frac{D_2}{D_1}\right)^2 - 1\right)}}$$

where $\Delta P_{BD}$ is the pressure differential between the second and fourth points, and $\rho$ is the fluid density, $\mu = \rho V_B D_1 / Re$ where Re is the Reynolds number and $V_B$ is average velocity from the equation $$V_B = \frac{D_2^2}{D_1^2} \sqrt{\frac{2\Delta P_{BD}}{\rho\left(\left(\frac{D_2}{D_1}\right)^2 - 1\right)}}.$$

20. A method according to claim 19 wherein said density is determined by the equation:

$\rho = \Delta P_{DC}/gh$ where $\Delta P_{DC}$ is the pressure differential between said third and said fourth points, g is gravity, and h is the vertical spacing between the third and fourth points.

21. A method for determining the density and viscosity parameters of a fluid comprising the steps of:

flowing the fluid through a conduit having a constricted portion of a first diameter ($D_1$) and a full width portion of a larger second diameter ($D_2$);

determining the pressure of the fluid at a first point at the entry of said constricted portion;

determining the pressure of the fluid at a second point at the exit of said constricted portion;

determining the pressure of the fluid at a third point in said full width portion spaced from the exit of said constricted portion;

determining the pressure of the fluid at a fourth point spaced above and aligned with the third point; and determining the density and viscosity, respectively, in accordance with the following equations:

$\rho = \Delta P_{DC}/gh$ where $\Delta P_{DC}$ is the pressure differential between said third and said fourth points, g is gravity, and h is the vertical spacing between the third and fourth points, $\mu = \rho V_B D_1 / Re$ where Re is the Reynolds number, $V_B$ is average velocity from the equation $$V_B = \frac{D_2^2}{D_1^2} \sqrt{\frac{2\Delta P_{BD}}{\rho\left(\left(\frac{D_2}{D_1}\right)^2 - 1\right)}}$$

and $\Delta P_{BD}$ is the pressure differential between the second and fourth points.

* * * * *